United States Patent [19]

Lind

[11] Patent Number: 5,154,713
[45] Date of Patent: Oct. 13, 1992

[54] ENHANCING ABSORPTION RATES OF SUPERABSORBENTS BY INCORPORATING A BLOWING AGENT

[75] Inventor: Eric J. Lind, Naperville, Ill.

[73] Assignee: Nalco Chemical Company, Naperville, Ill.

[21] Appl. No.: 845,906

[22] Filed: Mar. 4, 1992

Related U.S. Application Data

[62] Division of Ser. No. 781,526, Oct. 22, 1991.

[51] Int. Cl.$^5$ .................. A61F 13/15; A61F 13/20
[52] U.S. Cl. .................................. 604/358; 210/691; 604/367; 521/92; 521/149
[58] Field of Search .............. 604/358, 367; 210/691; 521/92, 149

[56] References Cited

U.S. PATENT DOCUMENTS

| | | |
|---|---|---|
| 4,693,713 | 9/1987 | Chmelir et al. ............ 604/358 |
| 4,724,242 | 2/1988 | Vassileff .................... 604/358 |
| 4,762,888 | 8/1988 | Sun et al. .................. 604/358 |
| 5,061,487 | 10/1991 | Blank et al. ............... 604/358 |

*Primary Examiner*—Morton Foelak
*Attorney, Agent, or Firm*—Robert A. Miller; Joseph B. Barrett

[57] ABSTRACT

An improved superabsorbent polymer having increased rate of water absorption is obtained by the addition, preferably prior to polymerization, of a carbonate blowing agent to a monomer solution of the monomers used to form the superabsorbent polymer. Preferred monomers include (meth)acrylic acids, preferably partially neutralized prior to polymerization and appropriate cross-linking agents. The carbonate cross-linking agents are any carbonate salt soluble or dispersible in the monomer solution, prior to polymerization. The multivalent cationic salts of carbonate are preferred, especially the complex carbonates, for example, of magnesium.

3 Claims, No Drawings

ENHANCING ABSORPTION RATES OF SUPERABSORBENTS BY INCORPORATING A BLOWING AGENT

This application is a division of application Ser. No. 07/781,526, filed Oct. 22, 1991.

INTRODUCTION

This invention relates to improved superabsorbent polymer compositions and to a process for their preparation. These superabsorbent polymer compositions are normally formed by any number of methods, which methods can include but are not limited to polymerization in solution to form hydrogel polymer in a gel form, polymerization in water-in-oil latexes to form hydrogel dispersed superabsorbent polymers dispersed in an oil continuous phase, or polymerization using any technique that would derive and then essentially dry superabsorbent substantially water-insoluble, slightly cross-linked and partially neutralized hydrogel forming superabsorbent polymer composition. These hydrogel forming superabsorbent polymeric materials are useful as absorbents for water and/or for aqueous body fluids when the polymers are incorporated in absorbent structures, absorbent articles, and the like, such as products represented by disposable diapers, adult incontinence pads, sanitary napkins, and similar absorbent structures.

BACKGROUND OF THE INVENTION

The water insoluble hydrogel forming polymers are materials capable of absorbing large quantities of aqueous fluids, such as water, brines, and body fluids and wastes. Further, the superabsorbents are capable of retaining such absorbed fluids under moderate pressures. These materials are especially useful in absorbent articles, such as disposable diapers. These hydrogel forming absorbent materials normally are composed of polymers containing polymerizable unsaturated carboxylic acids or derivatives and salts thereof. These monomeric acids are represented by acrylic acid and/or acrylic acid salts, methacrylic acid and/or salts thereof, alkylacrylates, acrylamides, and the like. These polymers are rendered water insoluble by cross-linking using any number of cross-linking agents. These monomeric carboxylic acid monomers, and other such monomers useful in these superabsorbent polymers and the cross-linking agents which are useful agents have been described in the art, particularly by U.S. Pat. No. 4,654,039, Brandt, et. al., which patent is incorporated herein by reference.

PRIOR ART

In addition to the U.S. Pat. No. 4,654,039, cited and incorporated herein above, other U.S. patents representative of superabsorbent polymer formation are listed below:

U.S. Pat. No. 3,514,510, Hoffman, Jr.
U.S. Pat. No. 3,670,731, Harmon
U.S. Pat. No. 3,935,363, Burkholder, et al.
U.S. Pat. No. 4,062,817, Westerman
U.S. Pat. No. 4,064,071, Gilmour, et al.
U.S. Pat. No. 4,123,397, Jones
U.S. Pat. No. 4,286,082, Tsubakimoto, et al.
U.S. Pat. No. 4,340,706, Obayashi, et al.
U.S. Pat. No. 4,342,858, Herman, et al.
U.S. Pat. No. 4,354,487, Oczkowski, et al.
U.S. Pat. No. 4,410,571, Korpman
U.S. Pat. No. 4,446,261, Yamasaki, et al.
U.S. Pat. No. 4,654,393, Mikita, et al.
U.S. Pat. No. 4,698,404, Cramm, et al.
U.S. Pat. No. 4,703,067, Mikita, et al.
U.S. Pat. No. 4,766,173, Bailey, et al.
U.S. Pat. No. 4,929,717, Chmelir
U.S. Pat. No. 4,950,692, Lewis, et al.
U.S. Pat. No. 4,970,267, Bailey, et al.

Each of these U.S. patents listed above are incorporated herein by reference.

This list of patents does not, however, contain any reference to increasing the rate of water absorption by incorporating in the solution, prior to polymerization, a carbonate based blowing agent.

There is some art discussing foamed materials, which, with strong hydrolysis of oil soluble polyesters, become superabsorbent, i.e. U.S. Pat. No. 4,529,739, incorporated herein by reference. Also, a reference to the use of nitrogen blowing agents; Austrian patent 391,321B, Sep. 25, 1990, (At 88-2108, Aug. 29, 1988) has been abstracted. These nitrogen blowing agents use ammonium carbamate, and accumulate excess ammonia.

THE INVENTION

We have found a method of improving the speed and/or rate of water absorption of a dry superabsorbent substantially water-insoluble, slightly cross-linked, partially neutralized, hydrogel-forming polymer composition, which method comprises:

1. Adding to an aqueous monomer solution, prior to polymerization, which monomer solution contains at least 20% by weight of at least one monomer selected from the group consisting of acrylic acid, methacrylic acid, acrylamide, methacrylamide, and their water soluble salts thereof, and an effective water insolubilizing amount of a cross-linking agent, an effective microcellular forming amount of a carbonate blowing agent, thereby forming a carbonated monomer solution, and then
2. Dispersing or dissolving said carbonate blowing agent throughout the carbonated monomer solution, and then
3. Either simultaneously or immediately preceding or following step 2, initiating free radical polymerization at temperatures ranging from 0° C. to 20° C. thereby exothermically forming a cross-linked hydrogel polymer, in expanded gel form, containing the blowing agent and having a micro cellular hydrogel structure, and then
4. Chopping said hydrogel into gel pieces having a average diameter ranging from about 0.1 millimeters to about 5.0 centimeters, and then
5. Drying said gel pieces at temperatures ranging from about 85° C. to about 210° C., to form dried pieces and then grinding said dried pieces to a particle size ranging from about 0.050 mm to about 5.0 mm. thereby forming an improved dry superabsorbent particulate polymer having increased rate of water absorption.

The Monomers

Our method is practiced preferably using monomers in an aqueous solution, or monomers dissolved in water and then dispersed in a water-in-oil emulsion, which monomers are most preferably selected from the group consisting of acrylic acid, the water soluble salts of acrylic acid, methacrylic acid, the water soluble salts thereof, and admixtures thereof.

However, any olefinically unsaturated carboxylic acid and carboxylic acid anhydride monomers can be used to form the improved superabsorbent polymers of this invention and include the acrylic acids, or their anhydrides, typified by acrylic acid itself, methacrylic acid, ethacrylic acid, alpha-chloroacrylic acid, alpha-cyano acrylic acid, beta-methyl acrylic acid, and the like. In some situation, the term (meth)acrylic acid is used. This term represents the presence of acrylic acid alone, methacrylic acid alone, any admixture of these acids, and any water soluble salt of these acids, either alone or in any admixture. These unsaturated carboxylic acids can also include itaconic acid, citraconic acid, maleic acid, fumaric acid, maleic anhydride, and the like.

Also, other olefinic unsaturated monomer can also be used, such as the sulfonic acid monomers. These monomers can be chosen from, but are not necessarily limited to, vinyl sulfonic acids, allyl sulfonic acids, styrene sulfonic acid, the sulfo-acrylic and methacrylic acid esters, including sulfoethylacrylate, sulfoethylmethacrylate, and sulfopropylacrylate, sulfopropylmethacrylate. Also, the sulfo (meth)acrylamide materials, such as acrylamido N-methylene sulfonic acid, acrylamido-N-ethylene sulfonic acid, 2-acrylamido-2-methylpropane sulfonic acid, and the like are useful. Other olefinically unsaturated monomers, such as acrylamide, methacrylamide, and the like may also be useful in forming copolymers, which copolymers can be cross-linked by the described cross-linkers to form the polymeric superabsorbants.

The Cross-Linking Agents

These cross-linking agents can include, but are not necessarily limited to, compounds having at least two polymerizable double bonds, compounds having at least one polymerizable double bond and at least one functional group reactive with the acid containing monomer material, compounds having at least two functional groups reactive with the acid containing monomer material, and polyvalent metal compounds, which metallic cations can form ionic cross linkages. The cross-linking agents are particularly exemplified by materials containing at least two polymerizable double bonds including, but not limited to, di, tri, or polyvinyl compounds, such as divinyl benzene, divinyl toluene, or di, tri, or polyesters of unsaturated mono or poly carboxylic acids with polyols including, for example, di or tri acrylic acid esters of polyol, such as ethylene glycol, trimethylpropane, glycerine, or polyoxyethylene glycols. Other cross-linking agents can include alkylene bis-acrylamides, such as N, N-methylene-bis-acrylamide, and can include carbamyl esters obtained by reacting polyisocyanates with hydroxyl group containing monomers; di, tri, or poly allyl ethers of polyols; di, tri, or poly allyl esters of polycarboxylic acids, such as diallyl phthalate, diallyl adipate, and the like. Other cross-linkers include the esters of unsaturated mono or poly-carboxylic acids with mono-allyl esters of polyols, such as the acrylic acid ester of polyethylene glycol monoallyl ether, and di or triallyl amine, and the alkylene glycol diglycidyl ethers.

The cross-linking agent generally is present from about 0.005 weight percent of the total formulation to about 2.0 weight percent of the total formulation. Preferably, the cross-linking agent present from about 0.10 wt. percent to about 1.0 wt. percent based on the total monomer formulation.

The most preferred cross-linking agents are selected from the group consisting of N,N'-methylene bis-acrylamide, trimethylol propane triacrylate, diallylamine, triallylamine, ethylene glycol diglycidyl ether, or mixtures thereof.

The Improved Superabsorbent Polymer

The polymer is formed in solution, or in a water-in-oil emulsion. The superabsorbent polymer is preferably formed from a thin layer of the carbonated monomer solution, which has been dearated (purged of oxygen) to which is added the free radical initiator of choice.

As before, the catalyst, or mixture of catalysts, may be added to the monomer solution, or the carbonated monomer solution immediately before, simultaneously with, or immediately after the addition of the carbonate blowing agent. By immediately before, or after, we mean to add the catalysts within no more than five minutes before or fifteen minutes after the addition of the carbonate blowing agent. Simultaneous addition of both catalyst and the blowing agent, or addition of catalyst after the addition of blowing agent is preferred. Most preferred is the addition of catalyst following the formation of the carbonated blowing agent.

Initial temperatures of the carbonated monomer solution are from 0°–20° C. The thin layer solution is preferably deaerated and protected from air before polymerization, and after initiating polymerization by the addition of free radical initiators (or by ionizing radical forming radiation), the polymerization forms an aqueous hydrogel of the cross-linked, water insoluble polymer. The polymerization is exothermic, causing the gel temperature to increase from initial temperature of about 0° C. to 20° C. to temperatures of about 80°–110° C. The aqueous gel, in the presence of the carbonate blowing agent, as heating and polymerization occurs (polymerization is exothermic) develops essentially a microcellular hydrogel, since the carbonate blowing agent is releasing carbon dioxide gases, which hydrogel has dispersed in it dispersed gaseous bubbles of carbon dioxide.

The microcellular structure may appear cloudy, demonstrating relatively small dispersed gas bubbles, may appear opaque, normally representing somewhat larger gas bubbles, (or higher quantitities of $CO_2$), or may appear quite foamy, with volume increases in excess of ten-fold the initial volume of the carbonated monomer solutions. The microcellular gel volume increases can range from about 1.01 up to at least 10.0 times the volume of the original carbonated monomer solution, depending upon, primarily, the concentration of the carbonate blowing agent contained in the treated monomer solution.

The preferable hydrogel forming polymer materials are normally synthesized from aqueous solutions containing at least 20, and most preferably at least 30–40 weight percent solution of acrylic acid, methacrylic acid, mixtures thereof and/or their water soluble salts. These monomers or mixtures of these monomers are preferably dissolved in an aqueous solution, which solution also contains the cross-linking agent in appropriate amount. The aqueous solution, herein referred to as the monomer solution, normally contains at least 20 percent by weight total monomer content, preferably at least 25 percent by weight total monomer content, and most preferably at least 30–40 percent by weight total monomer content. This monomer solution also contains effective water insolubilizing amounts of the cross-linking agents mentioned above. These are selected most preferably from the group consisting of the bis-acrylamides, such as N-N'-methylene bis-acrylamide, the di, tri, or polyesters of unsaturated mono or polycarboxylic acid polyols, such as trimethylpropane triacrylate, or the di, or tri glycidyl ethers of polyols, such as ethylene glycol diglycidyl ether, or the multi-substituted allyl amines, such as diallyl amine and triallyl amine, or any combination thereof.

The polymerization is initiated with free radical initiators known to the artisan. These initiators may include, but are not limited to, peroxide or persulfate catalysts, azo catalysts, the so called redox catalysts, or any combination of these free radical initiators and the like.

The hydrogel material may be made from the free acid, or be made from partially neutralized monomers, or may, in fact, be partially or completely neutralized either before or after formation by addition of appropriate base materials, such as sodium hydroxide, ammonia, and the like. Any suitable basic salt forming cation including the alkaline metals, ammonia, or ammonium salts, and amines may be used for the purpose of neutralization.

It is preferred to have a degree of neutralization of the starting carboxylic acid monomers of at least 50 mole percent and up to about 60-80 mole percent. When appropriate, the degree of neutralization within the ranges above may be partially accomplished by the addition of the carbonate based blowing agents to be described later.

The Blowing Agents

The carbonate blowing agents may be any carbonate or bicarbonate containing salt, or mixed salt, and may include carbon dioxide as a gas or a solid, sodium carbonate, potassium carbonate, ammonium carbonate, magnesium carbonate, or magnesium (hydroxic) carbonates, calcium carbonate, barium carbonate, bicarbonates and hydrates of these, or other cations, as well as naturally occurring carbonates, such as dolomite, or mixtures thereof. These blowing agents released carbon dioxide when heated while dissolved or dispersed in the carbonated monomer solutions. A most preferred carbonate blowing agent is $MgCO_3$, which may also be represented by the formula; $(MgCO_3)_4 \cdot Mg(OH)_2 \cdot 5H_2O$. Another preferred agent is $(NH_4)_2CO_3$. The $MgCO_3$ and $(NH_4)_2CO_3$ may also be used in mixtures.

It is preferred to add from about 0.05 to about 2.5 weight percent blowing agent (based on total carbonated monomer solution weight). It is most preferred to add from about 0.2 weight percent to about 2.5 weight percent blowing agent. The blowing agents must be added prior to, or immediately after polymerization is initiated. The blowing agents are not effective if added after the polymer gel (hydrogel) is formed, nor is it effective added after chopping or drying the gelled polymer, as will be demonstrated in the later examples.

The preferred blowing agents are carbonate salts of multi-valent cations, such as Mg, Ca, Zn, and the like. Although certain of the multi-valent transition metal cations may be used, some of them, such as ferric cation, can cause color staining and may be subject to reduction-oxidation reactions or hydrolysis equilibria in water. This may lead to difficulties in quality control of the final polymeric product. Also, other multi-valent cations, such as Ni, Ba, Cd, Hg would be unacceptable because of potential toxic or skin sensitizing effects.

SUMMARY

Our method is primarily related to improving the rate of absorption by superabsorbent polymers, of synthetic urine, aqueous brines, or aqueous solutions, including biological fluids, such as urine, sweat, blood, and the like. The improved superabsorbents of our invention are preferably (meth)acrylic acid based superabsorbent polymers and our method of manufacturing these materials comprises the steps of dissolving at least one acrylic acid monomer, and/or partially neutralized salts thereof (preferably the sodium salts) in an aqueous solution, which solution also contains a cross-linking agent.

The monomer-crosslinker solution (referred to herein as the monomer solution) is then completed by adding to it an effective microcellular forming amount of a carbonate blowing agent, preferably in the concentration of from 0.05 to about 2.5 weight percent of the total solution weight, thereby forming a carbonated monomer solution.

A free radical catalyst, is added immediately prior to, coincident with or immediately following the addition of the blowing agent, which catalyst can be any free radical catalyst, or combination of catalysts, known in the art. This initiated carbonated monomer solution is then heated appropriately, often by the exothermic polymerization reaction, to complete polymerization. The temperatures of polymerization range from an initial temperature of about 0° C.-20° C. and are exothermic to temperature of about 80° C.-110° C.

Polymerizing this carbonated monomer solution forms a hydrogel, which hydrogel has a micro cellular structure dispersion of carbon dioxide formed in the gel by the decomposition of the carbonate blowing agent. This microcellular gel is then masticated by chopping, grinding, or otherwise forming gel pieces of said microcellular hydrogel, which microcellular gel pieces have particle diameter sizes ranging from about 0.1 millimeters to about 5.0 centimeters, preferably about 10 mm to about 2.0 cm. These masticated gel pieces are then dried at temperatures of from about 85° C. to about 210° C. to form a dry superabsorbent polymer which is then ground to a particle size having a diameter of from about 0.05 mm to about 5.0 mm, which ground superabsorbent, has improved rates of absorption of the aqueous body fluids and synthetic solutions above.

The improved dry superabsorbent polymer essentially retains the gel strength and water (brine or synthetic urine) capacity of base formulations made without the carbonate blowing agents.

EXAMPLES

To Exemplify our invention, the following examples are presented:

An aqueous formulation containing about 30-40 weight percent of a combination of acrylic acid and sodium acrylate (about 40/60-20/80) and containing from about 0.1 to 0.5 weight percent of an amine based cross-linking agent is formed. To this monomer solution is added the following carbonate blowing agents. (See Table I).

In separate tests, polymerization was initiated and completed, the resultant gel (absent blowing agent) or microcellular gel (in the presence of blowing agent) was ground and dried, and the superabsorbent characteristics measured, using standard tests for gel strength, 0.9% saline capacity, and swell rate.

The results are presented in Table I:

TABLE I

| Monomer/Carbonate Blowing Agent Solution | | Superabsorbent Characteristics | | |
|---|---|---|---|---|
| Polymer | Blowing Agent, % (based on solution) | Synthetic Swell Rate (seconds) | Urine Gel Strength 1000 dynes/cm² | 0.9% Saline Capacity g/g |
| 30/70 mole % (Acrylic Acid/ Sodium Acrylate) | — | 83 (average of 5 separate synthesis) | 74.4 | 28.1 |
| 30/70 mole % (Acrylic Acid/ Sodium Acrylate) | $(NH_4)_2CO_3$; 2.5% | 54 | 93.3 | 21.3 |
| 30/70 mole % (Acrylic Acid/ Sodium Acrylate) | $(MgCO_3)_4Mg(OH)_2 \cdot 5H_2O$; 2.5% | Reactor contents - APPEARED AS FOAM - no tests could be completed | | |
| 30/70 mole % (Acrylic Acid/ Sodium Acrylate) | $(MgCO_3)_4Mg(OH)_2 \cdot 5H_2O$; 0.5% | 61 | 85.9 | 25.9 |
| 30/70 mole % (Acrylic Acid/ Sodium Acrylate) | $(MgCO_3)_4Mg(OH)_2 \cdot 5H_2O$; 0.25% | 64 | 87.5 | 26.3 |
| 30/70 mole % (Acrylic Acid/ Sodium Acrylate) | $CaCO_3$; 0.25% | 84 | 82.9 | 26.9 |
| 30/70 mole % (Acrylic Acid/ Sodium Acrylate) | Ammonium Carbamate; 0.4% | 62 | 79.6 | 27.6 |

The results in Table 1 demonstrate that, compared to a blank superabsorbent (ave. of 5 samples) made from the same neutralized acrylic acid and cross-linking agent, the polymers containing the carbonate blowing agents provide for greatly increased swell rates, using a synthetic urine. Also, gel strength seemed to be improved, essentially with minimal effects on capacity.

The number of seconds required to absorb a preset amount of synthetic urine is a measure of the rate of water absorption. Decreasing time is a good result. Also, the final improved superabsorbent also maintains and improves gel strength, and saline capacity of the superabsorbents formed is essentially still acceptable.

To demonstrate the ineffectiveness of adding the carbonate blowing agents after polymer gel is formed, the following tests and results are provided in Table II:

TABLE II

| % Blowing Agent ($MgCO_3$) (based on wet gel weight) | Synthetic Swell Rate (seconds) | Urine Gel Strength 1000 dynes/cm² | 0.9% Saline Capacity g/g |
|---|---|---|---|
| Addition of Magnesium Carbonate* to Dried Base Superabsorbent | | | |
| None (50/50 mole % AA/NaAA Polymer) | 147 | 61.2 | 27.5 |
| 7.4% | 157 | 58.0 | 26.3 |
| 0.25% | 183 | 57.5 | 27.1 |
| Addition of Magnesium Carbonate to Wet Gel, Before Chopping | | | |
| 7.4% | 161 | 68.5 | 23.4 |
| 0.25% | 140 | 68.1 | 24.6 |
| Addition of Magnesium Carbonate to Chopped Wet Gel | | | |
| 7.4% | 162 | 66.2 | 23.5 |
| 0.25% | 110 | 59.0 | 26.9 |

*$(MgCO_3)_4Mg(OH)_2 \cdot 5H_2O$

As can be seen, addition of the carbonate blowing agents before polymerizing is necessary, since the addition after gel formation is ineffective in obtaining improved superabsorbent polymer.

The synthetic urine tested contains the following cations and anions or elements dissolved in water:

| Elements | Concentrations |
|---|---|
| $Na^+$ | 600–700 ppm |
| $Ca^{++}$ | 65–75 ppm |
| $Mg^{++}$ | 55–65 ppm |
| $K^+$ | 1100–1200 ppm |
| Phosphorus | 240–280 ppm |
| Sulfur | 450–500 ppm |
| Chloride | 1100–1300 ppm |
| Sulfate | 1300–1400 ppm |

Having described my invention, I claim:

1. A method of improving the rate of absorption of aqueous body fluids, including blood and urine, by (meth)acrylic acid based superabsorbent polymers, which comprises:
   1). Dissolving at least one (meth)acrylic acid monomer and/or its sodium salt and a cross-linking agent in an aqueous solution to form a monomer solution;
   2). Adding to the monomer solution a carbonate blowing agent in sufficient amount to form, when polymerized to a hydrogel, a microcellular expanded polymer gel; thereby forming a carbonated monomer solution; then;
   3). Initiating free radical polymerization by adding to the carbonated monomer solution either immediately before or immediately after, or simultaneously with the addition of the blowing agent, an effective amount of at least one free radical initiator and polymerizing at temperatures ranging from about 0° C. to about 100° C. to form a microcellular hydrogel; and then;
   4). Chopping or grinding said microcellular hydrogel into gel pieces having a particle diameter size ranging from about 0.1 mm to about 5.0 cm, and then;

5). Drying said gel pieces at temperatures ranging from about 85° C.-210° C. to form dry pieces which dry pieces are ground to a size of from 0.05 mm to 5.0 mm diameter to form an improved dry superabsorbent polymer; and then;

6). Exposing said improved dry superabsorbent polymers to aqueous body fluids, thereby achieving an improved rate of absorption of aqueous body fluids by (meth)acrylic acid based superabsorbents.

2. The method of claim 1 wherein the improved dry superabsorbent polymer is contained within an absorbent structure selected from the group consisting of a diaper, an incontinent brief; sanitary napkins, or a bandage.

3. The method of claim 1 or 2 wherein the carbonated monomer solution containing (meth) acrylic acid monomer consists essentially of from 20–40 weight percent acrylic acid and from 60–80 weight percent sodium acrylate; and further, wherein the cross-linking agent is selected from methylene-bis-acrylamide, ethylene glycol diglycidyl ether, diallyl amine, triallyl amine, or mixtures thereof, and said cross-linking agent is present in the carbonated monomer solution at from 0.05 to about 0.5 weight percent; and further wherein the carbonate blowing agent is selected from the group consisting of $(NH_4)_2CO_3$, $MgCO_3$, $(MgCO_3)_4 \cdot Mg(OH)_2 \cdot 5H_2O$, or mixtures thereof, said blowing agent being present in the carbonated monomer solution at a concentration ranging from about 0.2 weight percent to about 2.5 weight percent; and further that the free radical initiator is chosen from at least one of the group consisting of hydrogen peroxide, sodium persulfate, azo catalysts, organic peroxides, sodium bisulfite, and peracetate catalysts.

* * * * *